United States Patent [19]

Horn

[11] Patent Number: 4,564,628
[45] Date of Patent: Jan. 14, 1986

[54] SUBSTITUTED 2-AMINOTETRALINS

[75] Inventor: Alan S. Horn, Noordhorn, Netherlands

[73] Assignee: Nelson Research & Development Co., Irvine, Calif.

[21] Appl. No.: 640,685

[22] Filed: Aug. 13, 1984

Related U.S. Application Data

[63] Continuation-in-part of Ser. No. 455,144, Jan. 3, 1983, abandoned.

[51] Int. Cl.$^4$ .................. A61K 31/38; C07D 333/12; C07D 333/22; C07D 307/02
[52] U.S. Cl. .................................. 514/438; 514/357; 514/415; 514/427; 514/399; 514/471; 514/521; 514/523; 549/74; 549/75; 549/77; 549/492; 549/494; 549/495; 546/329; 546/335; 546/334; 548/503; 548/561; 548/341; 560/138; 560/139; 560/110; 564/308; 260/465 E; 260/465 D
[58] Field of Search .................. 549/74, 75, 77, 492, 549/494, 495, ; 546/329, 335, 334; 548/341, 503, 561; 560/138, 139, 110; 564/308; 260/465 E, 465 D; 514/438, 357, 415, 427, 399, 471, 521, 523

[56] References Cited

U.S. PATENT DOCUMENTS 3,704,323 11/1979 Krapcho .......................... 260/256
4,314,082 2/1982 Stout .................................. 564/381

FOREIGN PATENT DOCUMENTS 1597140 12/1977 United Kingdom ................. 91/28

OTHER PUBLICATIONS

Hacksell et al., "N-Alkylated 2-Aminotetralins: Central Dopamine Receptor Stimulating Activity", Journal of Medicinal Chemistry, vol. 22, No. 12, 1979.
Sumners, et al., "Neurochemical and Behavioral Profiles of Five Dopamine Analogues", Archives of Pharmacology, Spring, 1981.
Feenstra et al., "Effect of Dihydroxy-2-Aminotetralin Derivatives on Dopamine Metabolism in the Rat Striatum", Archives of Pharmacology, Spring, 1980.
McDermed et al., "Synthesis and Pharmacology of Some 2-Aminotetralins. Dopamine Receptor Agonists.", Journal of Medicinal Chemistry, vol. 18, No. 4, 1975.
McDermed et al., "Synthesis and Dopaminergic Activity of (±)-, (+)-, and (−)-2-Dipropylamino-5-Hydroxy, etc . . . ", Journal of Medicinal Chemistry, vol. 19, No. 4, 1976.

Primary Examiner—Alan Siegel
Attorney, Agent, or Firm—Knobbe, Martens, Olson & Bear

[57] ABSTRACT

Novel compounds useful as dopamine receptor agonists for the treatment of various diseases of the central nervous system such as Parkinson's disease and related disorders having the structural formula

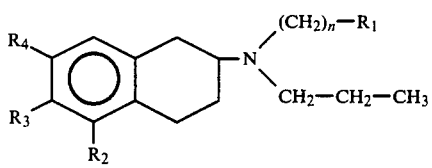

where $R_2$, $R_3$ and $R_4$ are each selected from the group consisting of H, and OA; A is H or

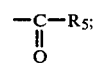

$R_5$ is selected from the group consisting of alkyl and aromatic residues; n is 2 or 3; and $R_1$ is selected from the group consisting of 3-hydroxyphenyl, 4-hydroxyphenyl, 3-pyridyl, 4-pyridyl,

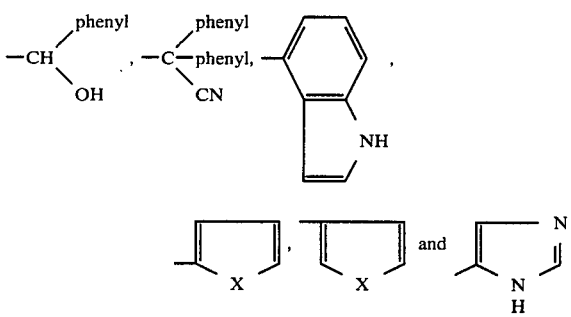

where X is S, O or NH; and pharmaceutically acceptable salts thereof. Also disclosed is a method for inducing a dopaminergic response in a patient by administering a pharmacologically-effective amount of one of the foregoing compounds.

17 Claims, No Drawings

SUBSTITUTED 2-AMINOTETRALINS

BACKGROUND OF THE INVENTION

This application is a continuation in part of Ser. No. 455,144, filed 1/3/83, now abandoned.

FIELD OF THE INVENTION

The invention relates generally to substituted 2-amino-tetralins and to processes for preparing such compounds. More particularly, the invention relates to compounds for therapeutic use, in particular in treating disorders of the central nervous, cardiovascular and endocrine systems.

BACKGROUND OF THE PRIOR ART

It is known that various hydroxylated 2-amino-tetralins of the general formula

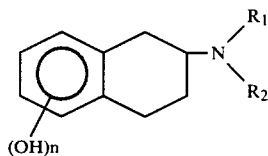

(OH)n where $R_1$ and $R_2$ are saturated alkyl groups and n is 1 or 2, are dopamine receptor agonists (Mc Dermed et al., J. Med. Chem. 18, 362 (1975); Feenstra et al., Arch. Pharmacol. 313, 213 (1980)).

SUMMARY OF THE INVENTION

We have now discovered novel compounds having the structural formula

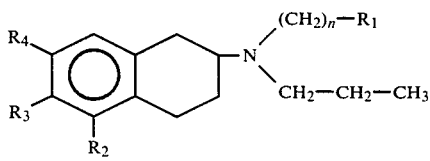

where $R_2$, $R_3$ and $R_4$ are each selected from the group consisting of H, and OA; A is H or

$R_5$ is selected from the group consisting of alkyl and aromatic residues, and $R_1$ is selected from the group consisting of 3-hydroxyphenyl, 4-hydroxyphenyl, 3-pyridyl, 4-pyridyl,

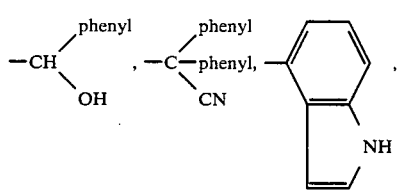

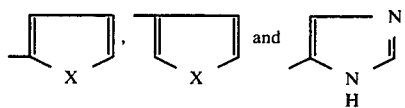

where X is S, O or NH; with the proviso that at least one of $R_2$, $R_3$ and $R_4$ is H, that at least one of $R_2$, $R_3$ and $R_4$ is not H, and that $R_2$ and $R_4$ are not both OA.

The compounds are useful as dopamine and D-2 receptor agonists for the treatment of disorders of the central nervous, cardiovascular and endocrine systems such as Parkinson's disease and related disorders, hypertension and hyperprolactinemia.

DETAILED DESCRIPTION OF THE INVENTION

The compounds described above may be prepared by the general methods outlined below. The numerical references in parenthesis following intermediates refer to numbered structural formulas below.

The esters and acid addition salts of the compounds of the general formula are prepared in the conventional manner. As acid addition salts, the salts derived from a therapeutically acceptable acid such as hydrochloric acid, acetic acid, propionic acid and, more particularly, from a di- or polybasic acid such as phosphoric acid, succinic acid, maleic acid, fumaric acid, citric acid, glutaric acid, citraconic acid, glutaconic acid, tartaric acid, malic acid, and ascorbic acid can be used.

METHOD I

The β-tetralone (1) is condensed with a primary amine in the presence of an acid catalyst such as TsOH. The resulting intermediate is then reduced (e.g. with $H_2/PtO_2$, $NaBH_3CN$ etc.) to yield the secondary amine (2). This is then acylated with propionyl chloride to give the amide (3). This amide is then reduced to the tertiary amine and the latter is demethylated with HBr or $BBr_3$ (depending on the nature of group $R_1$) to yield the phenol or catechol of general structure (4).

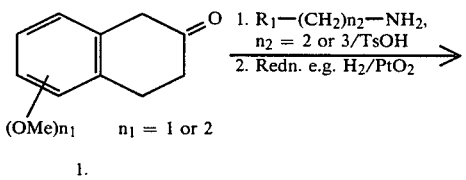

1.

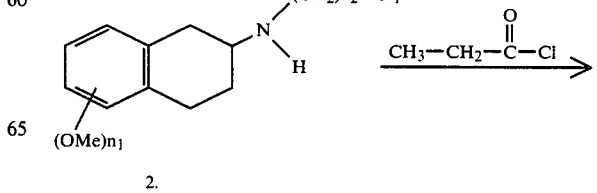

2.

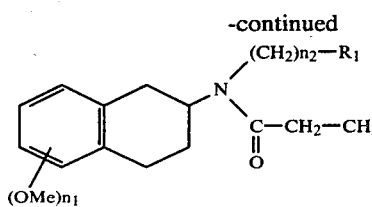

3.

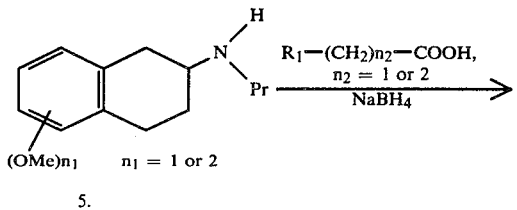

5.

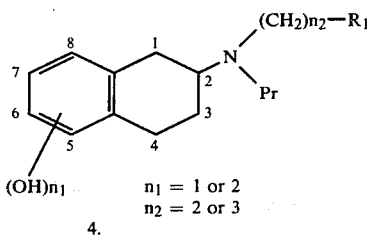

$n_1 = 1$ or $2$
$n_2 = 2$ or $3$

4.

METHOD II

Compound (5) is prepared by known methods, such as by condensation with propylamine followed by reduction. The intermediate (5) can be converted to compound (6) two ways:

A. via acylation with an acid chloride followed by reduction with LiAlH$_4$; or
B. via direct alkylation with the appropiate alkyl halide. Compound (4) is prepared from compound (6) by treatment with HBr or BBr$_3$.

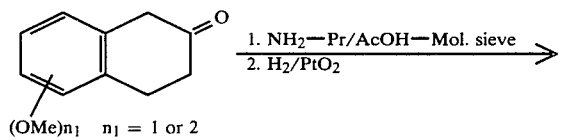

1.

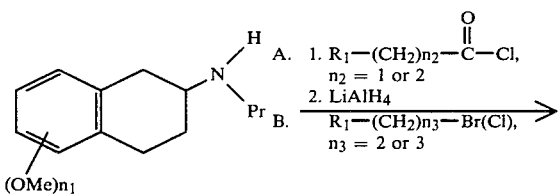

5.

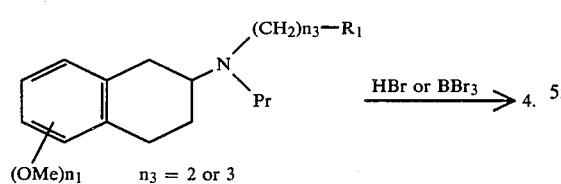

6.

METHOD III

Compound (5) is treated with the appropriate carboxylic acid and sodium borohydride to compound (6) in one step. (c.f. Hacksell et al., J. Med. Chem. 22, 1469, 1979). Compound (6) is converted to compound (4) as before; i.e., with HBr or BBr$_3$.

The prodrugs of these compounds where A is

may be prepared by treating the compound with the desired corresponding acid chloride (Horn et al., J. Med. Chem. 25, 993, 1982).

A preferred embodiment of this invention is a method of treatment which comprises inducing a dopaminergic response by administering a therapeutically effective amount of one of the foregoing compounds to a patient. In general, a pharmacologically-effective daily dose can be from 0.01 mg./kg. to 100 mg./kg. per day, and preferably from about 0.1 mg./kg. to 25 mg./kg. per day, bearing in mind, of course, that in selecting the appropriate dosage in any specific case, consideration must be given to the patient's weight, general health, metabolism, age and other factors which influence response to the drug. A particularly preferred dose is 1.0 mg./kg. per day.

Another embodiment of this invention is the provision of pharmaceutical compositions in dosage unit form which comprise from about 1 mg. to 500 mg. of a compound of the above formula.

The pharmaceutical composition may be in a form suitable for oral use, for example, as tablets, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents, and preserving agents in order to provide a pharmaceutically elegant and palatable preparation. Tablets contain the active ingredient in admixture with non-toxic pharmaceutically acceptable excipients which are suitable for manufacture of tablets. These excipients may be, for example, inert diluents, for example calcium carbonate, sodium carbonate, lactose, calcium phosphate, or sodium phosphate; granulating and disintegrating agents, for example maize starch, or alginic acid; binding agents, for example starch, gelatine, or acacia; and lubricating agents, for example magnesium stearate, stearic acids, or talc. The tablets may be uncoated or they may be coated by known techniques to delay disintegration and absorption in the gastrointestinal tract and thereby provide a sustained action over a longer period.

Formulations for oral use may also be presented as hard gelatine capsules wherein the active ingredient is mixed with an inert solid diluent, for example calcium carbonate, calcium phosphate, or kaolin, or as soft gelatine capsules wherein the active ingredient is mixed with an oil medium, for example arachis oil, liquid paraffin, or olive oil.

Aqueous suspensions contain the active compound in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth, and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol, for example polyoxyethylene sorbitol monooleate, or condensation product of ethylene oxide with partial esters derived from fatty acids and hexitol anhydrides, for example polyoxyethylene sorbitan monooleate. The said aqueous suspensions may also contain one or more preservatives, for example ethyl, n-propyl, or p-hydroxy benzoate, one or more coloring agents, one or more flavoring agents, and one or more sweetening agents, such as sucrose, saccharin, or sodium or calcium cyclamate.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, flavoring, and coloring agents, may also be present.

Syrups and elixirs may be formulated with sweetening agents, for example glycerol, sorbitol or sucrose. Such formulations may also contain a demulcent, a preservative, and flavoring and coloring agents. The pharmaceutical compositions may be in the form of a sterile injectable preparation, for example as a sterile injectable aqueous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol.

The pharmaceutical compositions may be tableted or otherwise formulated so that for every 100 parts by weight of the composition there are present between 5 and 95 parts by weight of the active ingredient and preferably between 25 and 85 parts by weight of the active ingredient. The dosage unit form will generally contain between about 1 mg. and about 100 mg. of the active ingredient of the formula stated above.

From the foregoing formulation discussion it is apparent that the compositions of this invention can' be administered orally or parenterally. The term parenteral as used herein includes subcutaneous injection, intravenous, intramuscular, or intrasternal injection or fusion techniques.

The invention is further illustrated by the following Examples.

EXAMPLE I

Preparation of 7-hydroxy-2-(N-n-propyl-N-2-thienylethyl)-aminotetralin

This compound was prepared according to Method I.

7-Methoxy-2-tetralon (3.75 g) and $\beta$(2-thienyl)ethylamine (3.27 g were dissolved in 50 ml dry toluene and p-toluenesulfonic acid (0.19 g) was added. This mixture was refluxed under an atmosphere of nitrogen for 2.5 hr. with continual removal of water (Dean-Stark method). The toluene was then removed under reduced pressure and the residue was dissolved in a mixture of methanol (4 ml) and T.H.F. (60 ml). The pH of this mixture was adjusted to approximately 5 by addition of HCl-ether. Sodium cyanoborohydride (1.16 g) was then added and the mixture was stirred under nitrogen gas at room temperature for 2 hr. The solvents were then removed under reduced pressure and the residue was dissolved in ether (50 ml) and extracted with water (50 ml). This water layer was re-extracted with ether (50 ml). The combined ether fractions were washed with a saturated sodium chloride solution (50 ml) and the ether layer was then dried over anhydrous $MgSO_4$. Removal of the ether under reduced pressure yielded 6.96 g of the free base, which was then converted to a HCl salt (6.11 g, 90%). Recrystallization from ethanol/ether produced an analytical sample, m.p. 224°–225° C.

The HCl salt (3.40 g) of the above secondary amine was dissolved in dichloromethane (40 ml) and triethylamine (2.52 g) was added. To this stirred solution at room temperature propionyl chloride (1.14 ml) was added in a dropwise fashion. During the whole of the above operation the temperature of the solution was kept at 5° C. This mixture was then stirred for a further 30 min. after the completion of the addition of propionyl chloride. The reaction mixture was then filtered and the filtrate was evaporated under reduced pressure. Ether-HCl was then added and the resulting precipitated amine hydrochlorides were filtered off and discarded. The ether solution was then reduced to dryness to yield the intermediate amide (2.75 g, 76%).

The above amide was dissolved in T.H.F. (25 ml) and this was added slowly to a mixture of $LiAlH_4$ (0.50 g) in T.H.F. (40 ml) under nitrogen gas. After refluxing for 3 hr. the mixture was allowed to cool, then water (3.0 ml) and a 15% NaOH solution (2.75 ml) and then additonal water (3×3 ml) was added. The solution was filtered off and the T.H.F. fraction was reduced to dryness. The residue was dissolved in ether (50 ml) and extracted with water (20 ml). After drying over anhydrous $MgSO_4$ the ether layer was evaporated to yield the free base (2.06 g). Conversion to an HCl salt produced a while solid (1.80 g, 72%) which after recrystallization yielded an analytical sample, m.p. 159°–160° C.

The above product (270 mg) was dissolved in dry dichloromethane and cooled to about −30° C. and 1N BBr$_3$ (7 ml) was added via a syringe. The mixture was stirred for about 2 hr. at this temperature and then for a further 2 hr. at room temperature. Sufficient methanol was then added to produce a clear solution. It was then extracted with a saturated solution of NaHCO$_3$ (15 ml) and water (20 ml). The organic layer was separated and dried over anhydrous MgSO$_4$. Reduction to dryness and conversion to an HCl salt yielded 190 mg (73%) of a white solid. The structure was confirmed by IR, MS, NMR and elemental analyses.

EXAMPLE II

Preparation of 5-hydroxy-2-(N-n-propyl-N-2-thienylethyl)-aminotetralin

This compound was prepared according to Method I.

5-Methoxy-2-tetralon (9.0 g, 51 mmol) and β(2-thienyl)ethylamine (7.8 g, 62 mmol) were dissolved in dry toluene (225 ml) and p-toluenesulfonic acid (0.19 g) was added. This mixture was refluxed under an atmosphere of nitrogen for 2.5 hr. with continual removal of water (Dean-Stark method). The toluene was then removed under reduced pressure and the residue was dissolved in a mixture of methanol (15 ml) and T.H.F. (225 ml). The pH of this mixture was then adjusted to approximately 5 by the addition of HCl-ether. Sodium cyanoborohydride (2.0 g, 32 mmol) was then added and the mixture was stirred under nitrogen gas at room temperature for 2 hr. The solvents were then removed under reduced pressure and the residue was dissolved in ether (50 ml) and extracted with water (50 ml). This water layer was re-extracted with ether (50 ml). The combined ether fractions were washed with a saturated NaCl solution (50 ml) and the ether layer was dried over anhydrous MgSO$_4$. Removal of the ether yielded an oil which on distillation under reduced pressure (0.03 mm Hg; 155°-160° C.) gave 9.8 g (67%) of the free base. Conversion to an HCl-salt gave an analytical sample, m.p. 201°-202° C.

The above free base (5.1 g, 17.8 mmol) was dissolved in dichloromethane (40 ml) containing triethylamine (2.0 g) and to this stirred solution at 5° C. propionyl chloride (1.85 g, 20.0 mmol) was added in a dropwise manner. After the completion of the latter addition the mixture was stirred for a further 30 min. Most of the dichloromethane was then removed under reduced pressure and ether-HCl was added. The resulting precipitated amine hydrochlorides were filtered off and discarded. The ether solution was then reduced to dryness to yield the intermediate amide (5.9 g).

The amide (5.9 g, 17.2 mmol) was dissolved in dry T.H.F. (50 ml) and this was added slowly to a suspension of LiAlH$_4$ (1.0 g, 26.3 mmol) in dry T.H.F. (75 ml) under an atmosphere of nitrogen. After refluxing for 3 hr. the mixture was allowed to cool and then water (5.0 ml) and a 15% NaOH solution (5.0 ml) and then additional water (3×5 ml) was added. The solution was filtered off and the T.H.F. fraction was reduced to dryness. The residue was dissolved in ether (100 ml) and extracted with water (50 ml). After drying over anhydrous MgSO$_4$ the ether layer was reduced to dryness yielding the free base (5.0 g, 85%). An analytical sample of HCl salt had a m.p. of 148°-150° C.

The above product (500 mg) was dissolved in dry dichloromethane and cooled to about −30° C. and then 1N BBr$_3$ (7 ml) was added via syringe. The mixture was stirred for 2 hr. at this temperaure. Sufficient methanol was then added to produce a clear solution. It was then extracted with a saturated solution of NaHCO$_3$ (15 ml) and water (20 ml). The organic layer was dried over anhydrous MgSO$_4$. Reduction to dryness and conversion to a HCl salt yielded 300 Mg (62.5%) of a white solid. The structure was confirmed by IR, MS, NMR and elemental analyses.

EXAMPLE III

Preparation of 5-hydroxy-2-(N-n-propyl-N-2-thienylethyl)-aminotetralin hydrochloride This compound was made according to Method III.

1.69 g of 5-methoxy-2(N-propylamino)tetralin, 2.09 g of 2-thiophene acetic acid and 1.089 g of trimethylamineborane were dissolved in 100 ml of dry xylene and refluxed under nitrogen for 18 hours. Work up and acidification with HCl gave 1.469 g of hydrochloride salt in 54% yield, m.p. 147°-148°.

1.059 g of the above salt was dissolved in 10 ml of dichloromethane and this was added dropwise to 16.2 millimole of BBr$_3$ in 48 ml of dichloromethane under nitrogen at 25° C. This mixture was stirred for 20 minutes. Work up and salt formation gave 860 mg (90%) of 5-hydroxy-2-(N-n-propyl-N-2-thienylethyl)aminotetralin hydrochloride, m.p. 170°-173° C.

EXAMPLE IV

Preparation of 5-hydroxy-2-(N-n-propyl-N-3-thienylethyl)-aminotetralin hydrochloride This compound was made according to Method III.

The reaction was carried out under conditions identical to those of Example III, employing 1.69 g of 5-methoxy-2(N-propylamino)tetralin, 2.09 g of 3-thiophene acetic acid and 1.089 g of trimethylamine-borane. Yield of 5-methoxy-2-(N-n-propyl-N-3-thienylethyl)-aminotetralin hydrochloride was 1.869 (62%), m.p. 149°-150° C.

500 mg of the above salt in 5 ml of dichloromethane was added to 8.1 millimole of BBr$_3$ in 25 ml of dichloromethane as outlined in Example III. Work up gave 430 mg (90%) of 5-hydroxy-(N-n-propyl-N-3-thienylethyl)-amino-tetralin hydrochloride, m.p. 184°-187° C.

Although the invention has been illustrated by reference to specific compounds and examples, it will be appreciated that many other compounds are within the scope of the invention. Accordingly, it is intended that scope of the present invention be measured only with reference to the following claims and reasonable equivalents thereof.

What is claimed is:

1. A compound having the structural formula

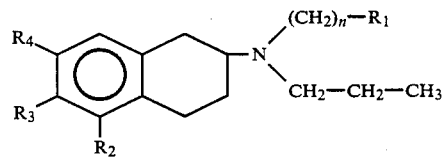

where $R_2$, $R_3$ and $R_4$ are each selected from the group consisting of H, and OA; A is H or

$R_5$ is selected from the group consisting of alkyl and aromatic residues; n is 2 or 3; and $R_1$ is selected from the group consisting of 3-pyridyl, 4-pyridyl,

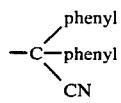

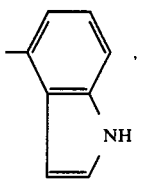

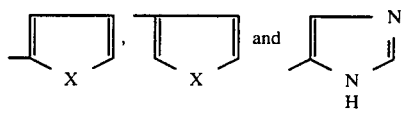

where X is S, O or NH, with the proviso that at least one of $R_2$, $R_3$ and $R_4$ is H, that at least one of $R_2$, $R_3$ and $R_4$ is not H and that $R_2$ and $R_4$ are not both OA; and pharmaceutically-acceptable salts thereof.

2. The compound of claim 1, where $R_4$ is H and $R_2$ and $R_3$ are OH.

3. The compound of claim 1, where $R_2$ is H and $R_3$ and $R_4$ are OH.

4. The compound of claim 1, where $R_3$ and $R_4$ are H and $R_2$ is OH.

5. The compound of claim 1, where $R_2$ and $R_3$ are H and $R_4$ is OH.

6. The compound of claim 1, where n is 2.

7. The compound of claim 1, where $R_1$ is

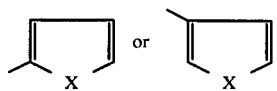

8. The compound of claim 1, where $R_1$ is selected from the group consisting of 3 pyridyl, 4 pyridyl,

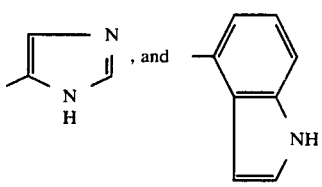

9. 7-Hydroxy-2-(N-n-propyl-N-2-thienylethyl-)aminotetralin and pharmaceutically-acceptable salts thereof.

10. 5-Hydroxy-2-(N-n-propyl-N-2-thienylethyl)-aminotetralin and pharmaceutically-acceptable salts thereof.

11. 5-Hydroxy-2-(N-n-propyl-N-3-thienylethyl)-aminotetralin and pharmaceutically-acceptable salts thereof.

12. A method, comprising:
   inducing a dopaminergic response in a patient by administering a pharmacologically-effective amount of a compound of claim 1.

13. The method of claim 12, wherein the compound is a compound of claim 7.

14. The method of claim 12, wherein the compound is a compound of claim 8.

15. The method of claim 12, wherein the compound is a compound of claim 9.

16. The method of claim 12, wherein the compound is a compound of claim 10.

17. The method of claim 12, wherein the component is a compound of claim 11.

* * * * *